United States Patent
Renner et al.

(10) Patent No.: US 6,188,788 B1
(45) Date of Patent: Feb. 13, 2001

(54) AUTOMATIC COLOR SATURATION CONTROL IN VIDEO DECODER USING RECURSIVE ALGORITHM

(75) Inventors: Karl Renner, Dallas; Weider Peter Chang, Hurst, both of TX (US)

(73) Assignee: Texas Instruments Incorporated, Dallas, TX (US)

( * ) Notice: Under 35 U.S.C. 154(b), the term of this patent shall be extended for 0 days.

(21) Appl. No.: 09/196,825

(22) Filed: Nov. 20, 1998

Related U.S. Application Data

(60) Provisional application No. 60/069,153, filed on Dec. 9, 1997.

(51) Int. Cl.[7] ................................................. G06K 9/00
(52) U.S. Cl. ............................................ 382/167; 382/173
(58) Field of Search ..................................... 382/162, 163, 382/164, 165, 166, 167, 168, 169, 170, 171, 172, 232, 245, 246, 247

(56) References Cited

U.S. PATENT DOCUMENTS

| | | | |
|---|---|---|---|
| 3,716,663 | * 2/1973 | Bolger ................................ | 178/54 |
| 4,463,371 | * 7/1984 | Lewis, Jr. ............................ | 358/13 |
| 4,635,102 | * 1/1987 | Bolger ................................ | 358/27 |
| 5,493,339 | * 2/1996 | Birch et al. ......................... | 348/461 |
| 5,585,929 | * 12/1996 | Young et al. ........................ | 386/1 |

* cited by examiner

Primary Examiner—Bijan Tadayon
Assistant Examiner—Amir Alavi
(74) Attorney, Agent, or Firm—Alan K. Stewart; Wade James Brady, III; Frederick J. Telecky, Jr.

(57) ABSTRACT

A method for automatic color gain control utilizes a plurality of process blocks which compare the measured burst amplitude with an ideal burst amplitude, and then generate necessary scaling factors to automatically control the gain. Each of the process blocks utilizes recursive relationships for accumulating values, which recursive relationships require no multiplications but, rather, require only additions and/or subtractions, which additions and/or subtractions require merely an adder with a change of sign. A scale value is generated which represents the ratio of the measure to ideal burst amplitude value, which is then utilized to generate Cr and Cb in a YCrCb digitized format. This is utilized to scale the U and the V values in a YUV digitized format.

7 Claims, 1 Drawing Sheet

AUTOMATIC COLOR SATURATION CONTROL IN VIDEO DECODER USING RECURSIVE ALGORITHM

This application claims priority under 35 USC § 119 (e)(1) of provisional application Ser. No. 60/069,153, filed Dec. 9, 1997.

TECHNICAL FIELD OF THE INVENTION

The present invention pertains in general to video decoders and, more particularly, to a video decoder operating in a YUV format with automatic color saturation control.

BACKGROUND OF THE INVENTION

In order to maintain a constant color level in the color output of a digital video decoder, automatic color saturation control is required. The goal of this automatic color saturation control is to maintain a constant color level as the strength of the signal varies over time. In general, color saturation control utilizes the amplitude of the color burst as a benchmark wherein the amplitude of the burst is measured and then compared with an ideal value. The ratio of the ideal burst amplitude to the measured burst amplitude is then computed and multiplied by the nominal cb and cr factors to produce multiplication factors, these factors being the color difference signals in a YCrCb color format. These multiplication factors are then applied to the demodulated U and V color difference signals within the video decoder in the YUV color format.

When implementing the above-noted algorithm, a number of divisions and multiplication operations are required to define the ratio. Typically, these division and multiplication operations are implemented by initially looking up an approximate value for the reciprocal of the measured value in a lookup table, and then refining it with the Newton Raphson recursive relation to improve the accuracy. This processing requires not only the use of a lookup table, but also multiplications which consumes a large portion of a simple microprocessor's throughput. The refine process can be eliminated at the expense of a course approximation. The lookup process itself involves a large amount of code which examines the measured burst amplitude and determines a range bin corresponding to an approximation to the ratio. The ratio must then be multiplied times the nominal cr and cb factors.

SUMMARY OF THE INVENTION

The present invention disclosed and claimed herein comprises a method and apparatus for controlling the color level in the color output of a video decoder. The color difference signals U and V associated with a YUV color format are first derived. The actual burst amplitude of the composite video color signal is then measured and compared to an ideal burst amplitude by determining the ratio of the measured burst amplitude to the ideal burst amplitude. This determined ratio is the scale factor which is determined utilizing a recursive relationship that requires only addition and subtraction. Nominal correction factors for the U and V color difference signals are then provided which represent correction factors therefor under normal conditions. These nominal correction factors are scaled with the scale factor utilizing a recursive relationship that represents the respective first and second nominal correction factors divided by the scale factor. This recursive relationship also utilizes only addition and subtraction operations to provide on the output thereof respective scaled first and second correction factors. The color difference signals are then scaled with the scaled correction factors.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
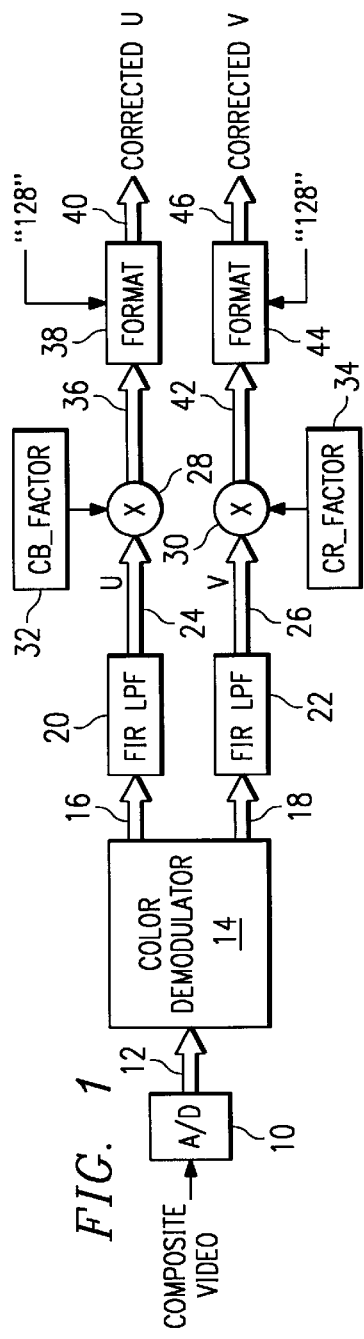
FIG. 1 illustrates a block diagram of a color demodulator for generating U and V components and the correction process for providing a corrected U and a corrected V output.

In general, digitizing of color involved converting the conventional color space RGB into one of a number of different color spaces. Typically, the RGB (red, green and blue) are the three color components that comprise a given computer image for a given pixel. Once the video data is digitized in real time by a video digitizer, it is typically represented in a number of formats, including the YUV video format and the YCrCb video format. The value of Y represents the luminescence which is basically intensity information required for a black and white system. Relative to the RGB system, the value of Y is represented as a scale factor of each of the RGB components. The value of U is the difference between the value of B and the value of Y by scale factor, and the value of V is the difference between the value of R and the value of Y by scale factor. Typically, the YUV color space is the basic color space utilized by PAL (phase alternation line), NTSC (National Television System Committee), and SECAM (Sequential Color with Memory) composite color video standards. The YCrCb color space is another color space digital component video standard that represents scaled and offset versions of the YUV color space. In general, Y is defined having a nominal range of 16 to 235 with cr and cb being defined to have a range of 16 to 240, with 128 equal to zero. There are several YCrCb sampling formats such as 4:4:4, 4:2:2, and 4:1:1. Another way to define the U and V color difference signals is by multiplying the demodulated U and V values by a cb_factor and a cr_factor, respectively, and adding a value of 128. The constant 128 is added to generate an 8-bit output to fall in the range between 16 and 240, where the value of 128 corresponds to a no color or black and white video condition. The equations for this would be as follows:

$$cb = \text{output } U = cb\_factor * \text{demodulated } U + 128 \quad (1)$$

$$cr = \text{output } V = cr\_factor * \text{demodulated } V + 128 \quad (2)$$

During automatic color saturation control, the color burst signal amplitude is measured and then compared against an ideal to determine the factors required to maintain a constant level of saturation, these being the cr_factor and the cb_factor. They are defined as follows:

$$cb\_factor = \left(\frac{\text{ideal burst amplitude}}{\text{measured burst amplitude}}\right) * \text{nominal } cb\_factor \quad (3)$$

$$cr\_factor = \left(\frac{\text{ideal burst amplitude}}{\text{measured burst amplitude}}\right) * \text{nominal } cr\_factor \quad (4)$$

If the color burst signal amplitude is weak, then the gain ratio is greater than one. If not, then it is less than one. It can be seen from the above-noted equation that the gain computation requires division and multiplication operations which could consume a significant amount of throughput in a simple microprocessor.

Referring now to FIG. 1, there is illustrated a block diagram of a conventional digital video system utilizing automatic color saturation control. The composite video signal, an analog signal, is digitized through the use of an analog-to-digital converter 10 and then input through an 8-bit bus 12 to a color demodulator 14. In the present invention, this color demodulator operates with a YUV format. The YUV format represents the composite video (CV) as follows:

$$CV = Y + U\sin\omega_{sc}t + V\cos\omega_{sc}t \quad (5)$$

The color demodulator 14 is operable to compute the various sin and cos operations and then divide the output thereof into two paths, one on a bus 16 and one on a bus 18 representing the U and the V components, respectively. These are passed trough low pass filters 20 and 22, respectively, which are Both Finite Impulse Response (FIR) low pass filters. This provides the filtered U and V signals on buses 24 and 26, respectively. The buses 24 and 26 are input to multiplication blocks 28 and 30, respectively, for multiplication by a cb_factor and a cr_factor, respectively, which are contained in registers 32 and 34, respectively. The output of block 28 is provided on a bus 36 to a format block 38 to provide a corrected U value on a bus 40. The format block 38 is operable to add the value of 128 to the product on the output of block 28. Similarly, the output of multiplication block 30 is provided on a bus 42 for input to a format block 44 to provide the corrected V output on a bus 46. Format block 44 allows the value of "128" to be added to the product output of the multiplication block 30. In general, this will provide the following functions:

$$c_r = cr\_factor * V + 128 \quad (6)$$

$$c_b = cb\_factor * U + 128 \quad (7)$$

In accordance with the present invention, the processing of the above-noted equations is performed with a recursive algorithm or recursive relations to compute the gain over many frames. The scale factor is computed by comparing the product of scale and ideal burst amplitude with 32 times the measured burst amplitude. The use of the factor 32 results in an integer value for scale. A delta value of +1 or −1 is selected based on the comparison. The negative feedback serves to force the comparator to be operate similar to the action in general operational amplifier applications.

Figure 2:
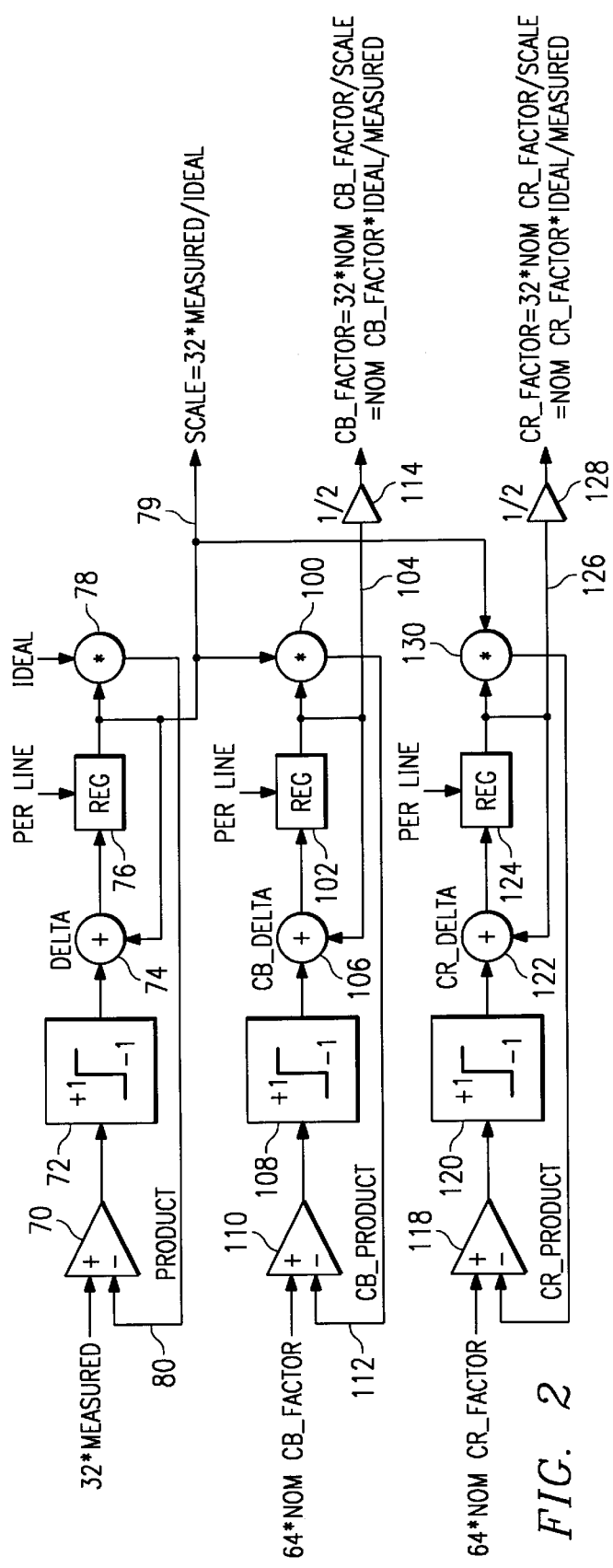
FIG. 2 illustrates a block diagram of the process for determining the cr_factor and the cb_factor.

Referring now to FIG. 2, there is illustrated a block diagram of the automatic color gain control processing block for implementing the recursive relations for generating the scale factors cb_factor and a cr_factor. The measured value of the burst amplitude is multiplied by a factor of 32, this basically being a shift left operation by five bits, therefore requiring no multiplication engine for this operation. This is input to the positive input of a comparator 70, the output thereof input to a block 72 which represents a delta value which is either a value of +1 or a value of −1. This generally is the output of the comparator 70. This delta value is then input to a summing block 74, the output thereof input to an accumulator register 76. This basically stores the scale factor. This is output on a line 78. The output of the register 76, the scale factor, is input to multiplication block 78, which receives a predetermined ideal burst amplitude for multiplication with the scale value. This represents a product on a line 80 that is input back to the negative input of the comparator 70.

In operation, the recursive relation will be as follows:

$$32 * measured = scale * ideal \quad (8)$$

$$scale = 32 * \frac{measured}{ideal} \quad (9)$$

The accumulation operation in the multiplication operation is only performed once per every scanned line. Therefore, there are "n" operations such that the delta value for delta$_n$ is always added to the scale value scale$_{n-1}$. Therefore, the following will represent how the multiplication is achieved in a recursive manner to determine the new product, product$_n$:

$$product_n = scale_n * ideal \quad (10)$$

$$product_n = (scale_{n-1} + delta_n) * ideal \quad (11)$$

$$product_n = scale_{n-1} * ideal + delta_n * ideal \quad (12)$$

$$product_n = product_{n-1} + delta_n * ideal \quad (13)$$

It can therefore be seen that the new product, product$_n$, is equal to the previous product, product$_{n-1}$, added to the product, delta$_n$*ideal. Since the value of delta$_n$ is either +1 or −1, this merely requires changing the sign of the ideal first amplitude value. Therefore, there is no multiplication involved; merely addition and subtraction.

The cb_product and a cr_product values that are required to perform the same computation for the cb_factor and a cr_factor are computed in a similar manner to that of the product$_n$. Since delta$_n$ and cb_delta$_n$ have values of +1 or −1, the computation requires an the accumulation of the appropriate signed values.

Referring further to FIG. 2, the scale value from register 76 is input to a multiplication block 100, the other input thereof output from a cb_factor accumulator register 102. The value stored herein comprises the previous cb_factor and the current cb_delta. This is achieved by feeding the input of the register 102 on a line 104 to the input of a summing junction 106, the other input thereof output from a delta block 108, which has a value of +1 or −1. The input to this block 108 is received from the output of a comparator 110. Comparator 110 receives on the positive input thereof the nominal cb_factor multiplied by a value of 64 and the negative input thereof comprising the output of the multiplication block 100 on a line 112.

The output of the accumulation register 76 comprises the scale value which is equal to the following:

$$scale = 32 * \frac{measured}{ideal} \quad (14)$$

To define the term cb_product, the following relationships will exist:

$$cb\_product = cb\_factor_n * scale_n \quad (15)$$

$$cb\_product = (cb\_factor_{n-1} + cb\_delta_n) * (scale_{n-1} + delta_n) \quad (16)$$

$$cb\_product_n = cb\_factor_{n-1} * scale_{n-1} + cb\_delta_n * scale_{n-1} + delta_n * cb\_factor_{n-1} + cb\_delta_n * delta_n \quad (17)$$

$$cb\_product_n = cb\_product_{n-1} + cb\_delta_n * scale_{n-1} + delta_{n-1} * cb\_factor_{n-1} + cb\_delta_n * delta_n \quad (18)$$

It can be seen from the above-noted equations that, to determine the value of cb_product$_n$, it is only necessary to know the previous product, cb_product$_{n-1}$ and the previous value of $scale_{n-1}$, in addition to the previous value of $cb\_factor_{n-1}$. Since the value of $cb\_delta_n$ is either + or –, there are no actual multiplications other than changing a sign. This will, therefore, result in the value stored in the register being the $cb\_factor_n$ being equal to:

$$2*cb\_\text{factor} = \frac{64*nom\ cb\_\text{factor}}{scale} = \frac{nom\ cb\_\text{factor}*ideal}{measured} \qquad (19)$$

In order to obtain the correct cb_factor, it is necessary to divide the output of the register 102 by a value of ½ with a divide operation that is represented by block 112; this is equivalent to a simple right shift by one bit. The calculation of the cr_factor is achieved in the same way. The nominal cr_factor is multiplied by a value of 64 and is then input to the positive input of a comparator 118, the output thereof providing the delta value in a block 120. This delta factor is the cr_delta factor, which is input into the summing block 122, the output thereof input to an accumulation register 124. The output of the accumulation register 124 and a line 126 comprises the other input to the summing block 122. This value on line 122 also represents the value of the cr_factor multiplied by a factor of 2, which is input to a divide-by-two (right shift by one bit) block 128 to provide the output cr_factor. The output of the accumulation register 124 also constitutes one input to a multiplication block 130, the other input thereof comprising the scale value from the register 76. The output of multiplication block 130 comprises the cr_product value which is input to the negative input of the comparator 118. The circuitry for calculating the cr_factor will operate similar to the above-noted one with cr_product being defined as follows:

$cr\_product_n = cr\_product_{n-1} + cr\_delta_n * scale_{n-1} + delta_n * cr\_factor_{n-1} + cr\_delta_n * delta_n$ \qquad (20)

This will result in a cr_factor which will be generated in accordance with the following relationship:

$$cr\_\text{factor} = 32 * \frac{nom\ cr\_\text{factor}}{scale} = \frac{nom\ cr\_\text{factor}*ideal}{measured} \qquad (21)$$

This is a recursive relationship which is performed once per each line in the video signal. As noted above, each of the accumulation registers 76, 102 and 124 accumulate a value only once per line. At time n=0, the cb_product and the cr_product values are initialized to 64*nominal cb_factor and 64*nomninal cr_factor. The algorithm requires a number of iterations to converge to a stable value. nis is illustrated in the following Table 1.

TABLE I

Automatic Color Saturation Algorithm Perfomance
ideal = 500 nominal cb factor = 444 cr factor = 315

| variable measured | scale | | cb_factor | | | cr_factor | | | |
|---|---|---|---|---|---|---|---|---|---|
| | float | calc | float | calc | error | float | calc | error | iter |
| 500 | 1.0 | 32 | 444.0 | 444 | 0.00 | 315.0 | 315 | 0.00 | 2 |
| 525 | 1.0 | 33 | 422.9 | 430 | -7.64 | 300.0 | 305 | -5.50 | 29 |
| 550 | 1.1 | 35 | 403.6 | 405 | -1.86 | 286.4 | 287 | -1.14 | 52 |
| 575 | 1.1 | 36 | 386.1 | 395 | -8.91 | 273.9 | 280 | -6.09 | 23 |
| 600 | 1.2 | 38 | 370.0 | 374 | -4.00 | 262.5 | 265 | -2.50 | 44 |
| 625 | 1.2 | 39 | 355.2 | 364 | -9.30 | 252.0 | 258 | -6.50 | 21 |
| 650 | 1.3 | 41 | 341.5 | 346 | "4.96 | 242.3 | 245 | -3.19 | 38 |

TABLE I-continued

Automatic Color Saturation Algorithm Perfomance
ideal = 500 nominal cb factor = 444 cr factor = 315

| variable measured | scale | | cb_factor | | | cr_factor | | | |
|---|---|---|---|---|---|---|---|---|---|
| | float | calc | float | calc | error | float | calc | error | iter |
| 675 | 1.4 | 43 | 328.9 | 330 | -1.61 | 233.3 | 234 | -1.17 | 34 |
| 700 | 1.4 | 44 | 317.1 | 323 | -5.86 | 225.0 | 229 | -4.00 | 17 |
| 725 | 1.5 | 46 | 306.2 | 309 | -2.79 | 217.2 | 219 | -1.76 | 30 |
| 750 | 1.5 | 47 | 296.0 | 302 | -6.50 | 210.0 | 214 | -4.50 | 15 |
| 500 | 1.0 | 32 | 444.0 | 444 | 0.00 | 315.0 | 315 | 0.00 | 2 |
| 475 | 0.9 | 31 | 467.4 | 458 | 8.87 | 331.6 | 325 | 6.08 | 31 |
| 450 | 0.9 | 29 | 493.3 | 489 | 3.83 | 350.0 | 347 | 2.50 | 64 |
| 425 | 0.9 | 28 | 522.4 | 507 | 15.35 | 370.6 | 360 | 10.59 | 37 |
| 400 | 0.8 | 26 | 555.0 | 546 | 9.00 | 393.8 | 388 | 5.75 | 80 |
| 375 | 0.8 | 24 | 592.0 | 592 | 0.00 | 420.0 | 420 | 0.00 | 94 |
| 350 | 0.7 | 23 | 634.3 | 617 | 16.79 | 450.0 | 438 | 11.50 | 53 |
| 325 | 0.6 | 21 | 683.1 | 676 | 6.58 | 484.6 | 479 | 5.12 | 120 |
| 300 | 0.6 | 20 | 740.0 | 710 | 30.00 | 525.0 | 504 | 21.00 | 69 |
| 275 | 0.6 | 18 | 807.3 | 789 | 18.27 | 571.7 | 560 | 12.73 | 160 |
| 250 | 0.5 | 16 | 888.0 | 888 | 0.00 | 630.0 | 630 | 0.00 | 200 |

Variables in the algorithm are first initialized, and then the measured inputs are increased, starting with the ideal value of 500. The number of iterations required for convergence of the cb_factor and cr_factor are determined before the next measured value is processed. Thereafter, the algorithm is reinitialized, and the measured input is decreased starting with the ideal 500. Due to the relatively slow response of the algorithm, it will track the average measure values. The program has been implemented as a C program, which is attached as Appendix A, which was utilized to generate the data illustrated in Table 1.

In summary, there has been provided a method for utilizing a recursive relationship to generate the necessary scaling actors to automatically compare the measured burst amplitude value to an ideal burst amplitude value and then vary the gain of the color computation to generate the color difference signals into a digitized format. This recursive relationship utilizes only a plurality of addition and/or subtractions requiring merely a sign change for given values.

Although the preferred embodiment has been described in detail, it should be understood that various changes, substitutions and alterations can be made therein without departing from the spirit and scope of the invention as defined by the appended claims.

What is claimed is:

1. A method for controlling the color level in the color output of a video decoder, comprising the steps of:
    deriving the color difference signals U and V in a YUV color format for a composite video signal;
    providing an ideal burst amplitude of the composite video color signal;
    measuring the actual burst amplitude of the composite video color signal;
    determining as a scale factor the ratio of the measured burst amplitude to the ideal burst amplitude of the composite video color signal with a recursive relationship requiring only addition and subtraction;
    determining a first and a second nominal correction factor for the U and V color difference signals, respectively, that represent a correction factor therefor,
    scaling the first and second nominal correction factors with the determined scale factor with a recursive relationship that represents the respective first and second nominal correction factors divided by the determined scale factor, which recursive relationship utilizes only addition and subtraction to provide on the output thereof respective scaled first and second correction factors, and scaling the color difference signals with the respective first and second scaled correction factors to provide scaled color difference signals U and V.

2. The method of claim 1, wherein each of the recursive relationships is an iterative relationship that is iterated once per every scan line in a frame of video of the composite video color signal.

3. The method of claim 1, wherein the recursive relationship for the step of determining the scale factor and the recursive relationships for the step of scaling the first and second correction factors are substantially the same.

4. The method of claim 3, wherein the recursive relationship includes the steps of:

storing an accumulated value representing the output of the recursive relationship as the ratio of two input values, a first value and a second value;

comparing the product of the stored accumulated value and the second input value with the first input value; and incrementing the accumulated value by +1 when the product is greater than the first value, and decrementing the accumulated value by −1 when the product is less than the first value, the steps of storing, comparing and incresmenting/decrementing realized with only addition and subtraction operations.

5. The method of claim 4, wherein the first value in the recursive relationship for the step of determining the scale factor is the measured burst amplitude, and the second value therein is the ideal burst amplitude.

6. The method of claim 4, where in the first value in the recursive relationship for the step of scaling the first and second correction factors is the first and second nominal correction factors, respectively, and the second value therein is the first and second scaled correction factors, respectively, which first and second scaled correction factors represent the ratio of the first and second nominal correction factors, respectively, with the determined scale factor.

7. An automatic color saturation control for controlling the color level in the color output of a video decoder, comprising:

means for deriving the color difference signals U and V in a YUV color format for a composite video signal;

means for providing an ideal burst amplitude of the composite video color signal;

means for measuring the actual burst amplitude of the composite video color signal;

means for determining as a scale factor the ratio of the measured burst amplitude to the ideal burst amplitude of the composite video color signal with a recursive relationship requiring only addition and subtraction;

means for determining a first and a second nominal correction factor for the U and V color difference signals, respectively, that represent a correction factor therefor;

means for scaling the first and second nominal correction factors with the determined scale factor with a recursive relationship that represents the respective first and second nominal correction factors divided by the determined scale factor, which recursive relationship utilizes only addition and subtraction to provide on the output thereof respective scaled first and second correction factors; and means for scaling the color difference signals with the respective first and second scaled correction factors to provide scaled color difference signals U and V.

* * * * *